United States Patent
Von Oepen et al.

(10) Patent No.: US 8,167,929 B2
(45) Date of Patent: May 1, 2012

(54) SYSTEM AND METHOD FOR DELIVERING A STENT TO A BIFURCATED VESSEL

(75) Inventors: Randolf Von Oepen, Los Altos, CA (US); Thomas Michael Rieth, Hirrlingen (DE); Lorcan James Coffey, Tubingen (DE); Richard Roy Newhauser, Redwood City, CA (US); Travis Richard Yribarren, San Mateo, CA (US)

(73) Assignee: Abbott Laboratories, Abbott Park, IL (US)

( * ) Notice: Subject to any disclaimer, the term of this patent is extended or adjusted under 35 U.S.C. 154(b) by 817 days.

(21) Appl. No.: 11/683,995

(22) Filed: Mar. 8, 2007

(65) Prior Publication Data

US 2007/0260217 A1 Nov. 8, 2007

Related U.S. Application Data

(60) Provisional application No. 60/780,752, filed on Mar. 9, 2006.

(51) Int. Cl.
*A61F 2/06* (2006.01)
*A61F 2/82* (2006.01)

(52) U.S. Cl. ..................................... 623/1.35; 623/1.11

(58) Field of Classification Search ................. 623/1.11, 623/1.12, 1.13, 1.16, 1.3, 1.31, 1.34, 1.35; 606/108, 194, 198
See application file for complete search history.

(56) References Cited

U.S. PATENT DOCUMENTS

| | | | |
|---|---|---|---|
| 4,877,031 A * | 10/1989 | Conway et al. | 606/194 |
| 4,909,258 A * | 3/1990 | Kuntz et al. | 600/435 |
| 4,994,071 A | 2/1991 | MacGregor | |
| 5,156,619 A | 10/1992 | Ehrenfeld | |
| 5,458,585 A | 10/1995 | Salmon et al. | |
| 5,496,365 A | 3/1996 | Sgro | |
| 5,507,767 A | 4/1996 | Maeda | |
| 5,571,073 A | 11/1996 | Castillo | |

(Continued)

FOREIGN PATENT DOCUMENTS

EP 0 492 361 7/1992

(Continued)

OTHER PUBLICATIONS

U.S. Appl. No. 11/683,999, mail date Feb. 19, 2010, Restriction Requirement.

(Continued)

*Primary Examiner* — Elizabeth Houston
(74) *Attorney, Agent, or Firm* — Workman Nydegger; Jonathan Feuchtwang

(57) ABSTRACT

A stent delivery catheter system for accurately positioning a stent in a bifurcated vessel is disclosed. The system includes a catheter having a terminal portion and distal tip that is placed in a main branch of the vessel proximate the bifurcation. A fixed guidewire is attached to distal tip. A port is defined in the terminal portion of the catheter. The port is aligned with an ostium of a side branch of the bifurcated vessel to allow the passage of a stent delivery device, such as a balloon catheter having a stent crimped thereon, into the side branch. Radiopaque bands are positioned on opposite ends of the port. A positioning balloon is included on a surface of the catheter opposite the port and is selectively inflatable to position the radiopaque bands adjacent the side branch ostium. The radiopaque bands are referenced to place the stent proximate the side branch ostium.

28 Claims, 11 Drawing Sheets

U.S. PATENT DOCUMENTS

| | | | |
|---|---|---|---|
| 5,643,340 | A | 7/1997 | Nunokawa |
| 5,741,429 | A | 4/1998 | Donadio, III et al. |
| 5,795,331 | A * | 8/1998 | Cragg et al. ............. 604/103.01 |
| 5,800,520 | A | 9/1998 | Fogarty et al. |
| 5,827,320 | A * | 10/1998 | Richter et al. ................ 606/194 |
| 5,830,155 | A | 11/1998 | Frechette et al. |
| 5,860,963 | A | 1/1999 | Azam et al. |
| 5,906,640 | A | 5/1999 | Penn et al. |
| 6,001,124 | A | 12/1999 | Bachinski |
| 6,165,195 | A * | 12/2000 | Wilson et al. ................ 606/194 |
| 6,179,878 | B1 | 1/2001 | Duerig et al. |
| 6,183,509 | B1 | 2/2001 | Dibie |
| 6,210,431 | B1 | 4/2001 | Power |
| 6,258,116 | B1 | 7/2001 | Hojeibane |
| 6,264,686 | B1 | 7/2001 | Rieu et al. |
| 6,475,209 | B1 | 11/2002 | Larson et al. |
| 6,491,719 | B1 | 12/2002 | Fogarty et al. |
| 6,500,147 | B2 | 12/2002 | Omaleki et al. |
| 6,527,790 | B2 * | 3/2003 | Chien et al. ................... 606/194 |
| 6,530,897 | B2 | 3/2003 | Lardeo |
| 6,666,884 | B1 | 12/2003 | Webster |
| 6,676,691 | B1 * | 1/2004 | Hosny ......................... 623/1.11 |
| 6,730,103 | B2 * | 5/2004 | Dakov ......................... 606/153 |
| 6,855,123 | B2 | 2/2005 | Nita |
| 7,105,020 | B2 | 9/2006 | Greenberg et al. |
| 7,169,176 | B2 | 1/2007 | Lauterjung |
| 7,252,679 | B2 | 8/2007 | Fischell et al. |
| 7,323,009 | B2 * | 1/2008 | Suhr et al. .................... 623/1.35 |
| 7,344,557 | B2 * | 3/2008 | Yadin ........................... 623/1.11 |
| 7,578,831 | B2 * | 8/2009 | von Oepen et al. ........... 606/194 |
| 2001/0027291 | A1 | 10/2001 | Shanley |
| 2002/0111665 | A1 | 8/2002 | Lauterjung |
| 2004/0158143 | A1 * | 8/2004 | Flaherty et al. ............... 600/407 |
| 2004/0193254 | A1 | 9/2004 | Greenberg et al. |
| 2004/0225345 | A1 | 11/2004 | Fischell et al. |
| 2005/0060027 | A1 | 3/2005 | Khenansho et al. |
| 2005/0084130 | A1 | 4/2005 | Yamagishi |
| 2005/0119606 | A1 | 6/2005 | Nita |
| 2006/0079956 | A1 * | 4/2006 | Eigler et al. ................ 623/1.35 |
| 2006/0100694 | A1 * | 5/2006 | Globerman ................ 623/1.35 |
| 2006/0282154 | A1 | 12/2006 | Oepen et al. |
| 2007/0088428 | A1 | 4/2007 | Teichman |
| 2007/0270933 | A1 | 11/2007 | Von Oepen |
| 2008/0046066 | A1 * | 2/2008 | Jenson et al. ................ 623/1.16 |

FOREIGN PATENT DOCUMENTS

| | | |
|---|---|---|
| EP | 1 293 178 | 3/1993 |
| EP | 0 891 751 | 1/1999 |
| EP | 1 512 380 | 3/2005 |
| WO | WO 97/07752 | 3/1997 |
| WO | WO 98/36709 | 8/1998 |
| WO | WO 02/13727 | 2/2002 |
| WO | WO 02/47591 | 6/2002 |
| WO | WO 03/088871 | 10/2003 |
| WO | WO 2005/084130 | 9/2005 |
| WO | PCT/US07/63704 | 3/2007 |
| WO | WO 2007/104051 | 9/2007 |
| WO | WO 2007/104056 | 9/2007 |

OTHER PUBLICATIONS

U.S. Appl. No. 11/683,999, filed Mar. 8, 2007.
U.S. Appl. No. 11/683,997, filed Mar. 8, 2007.
U.S. Appl. No. 12/782,399, filed May 18, 2010, Chan.
U.S. Appl. No. 60/780,752, filed Mar. 9, 2006, Von Oepen.
U.S. Appl. No. 11/683,997, mail date Apr. 27, 2010, Office Action.
U.S. Appl. No. 11/683,997, mail date Jul. 9, 2010, Office Action.
U.S. Appl. No. 11/683,999, mail date Apr. 28, 2010, Office Action.
U.S. Appl. No. 11/683,997, mail date Nov. 23, 2010, Office Action.
U.S. Appl. No. 11/683,999, mail date Oct. 27, 2010, Office Action.
U.S. Appl. No. 11/683,999, mail date Aug. 17, 2011, Office Action.
U.S. Appl. No. 11/683,999, mailed Jan. 26, 2012, Office Action.
U.S. Appl. No. 11/683,999, mailed Feb. 8, 2012, Office Action.

* cited by examiner

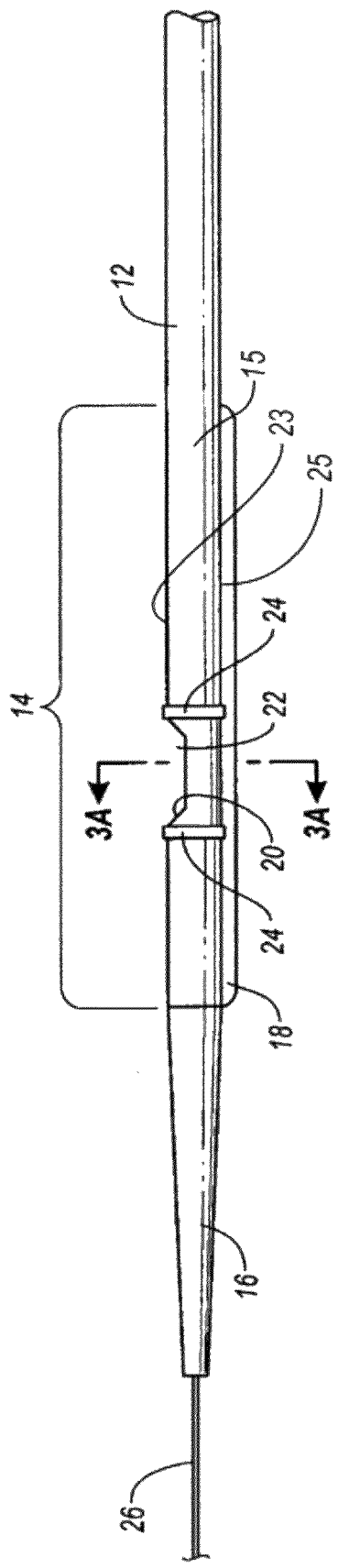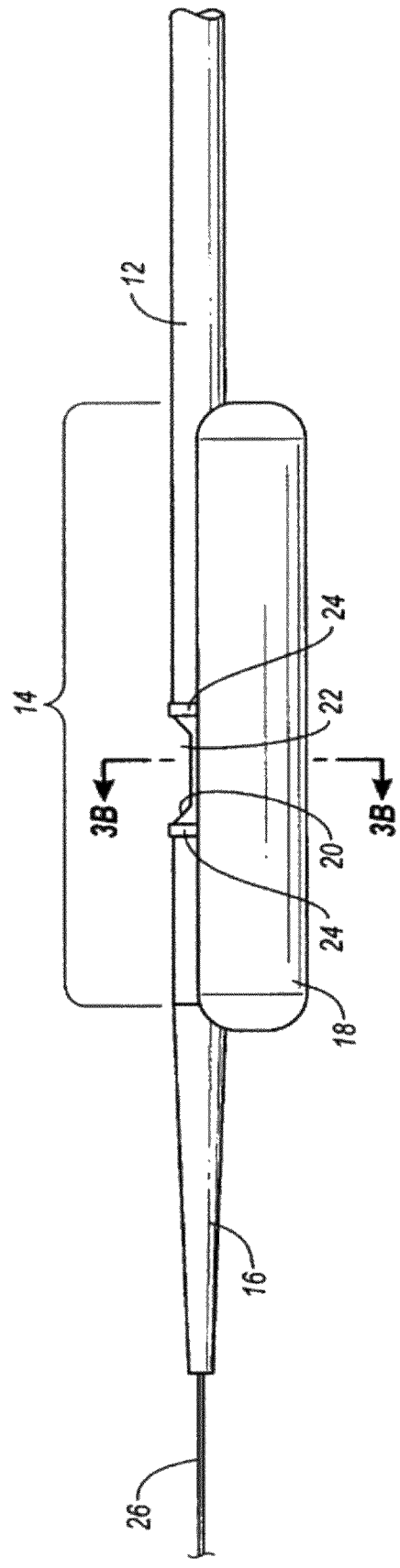

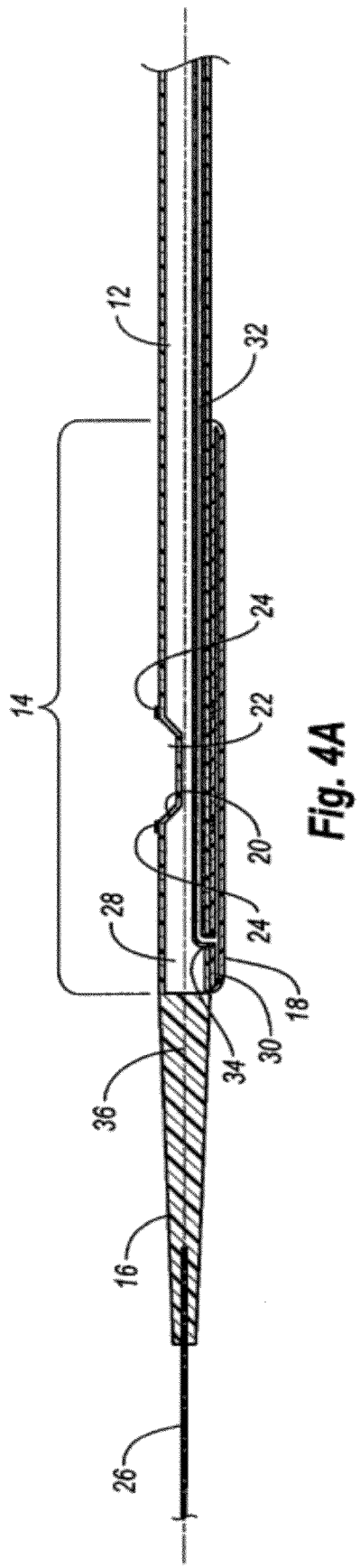
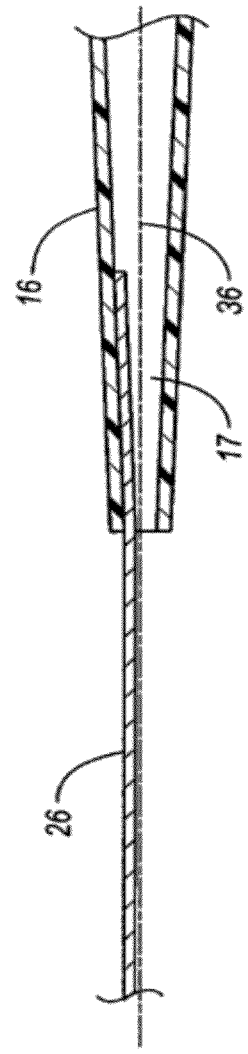
Fig. 4A
Fig. 4B

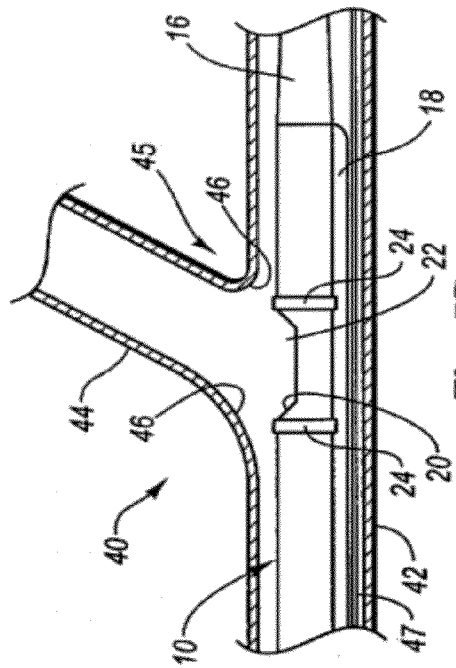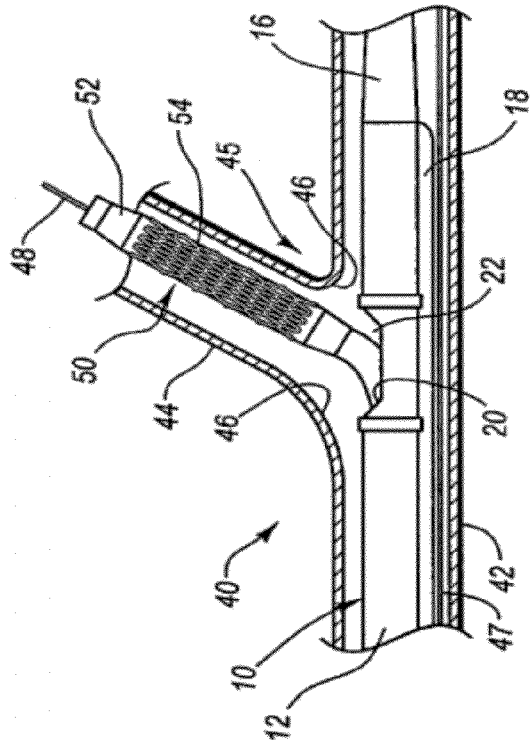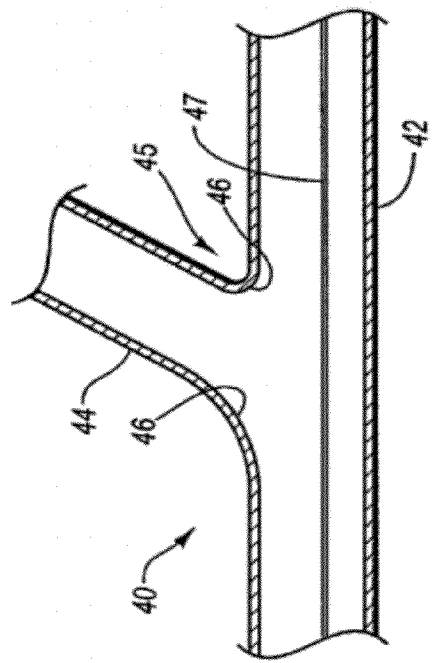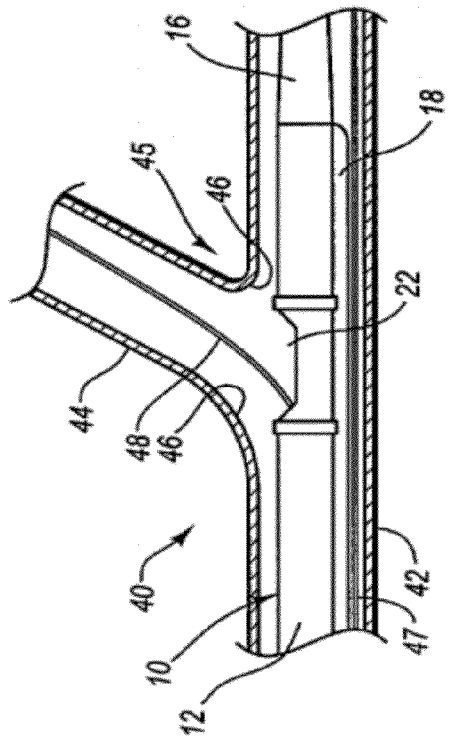
Fig. 5A
Fig. 5B
Fig. 5C
Fig. 5D

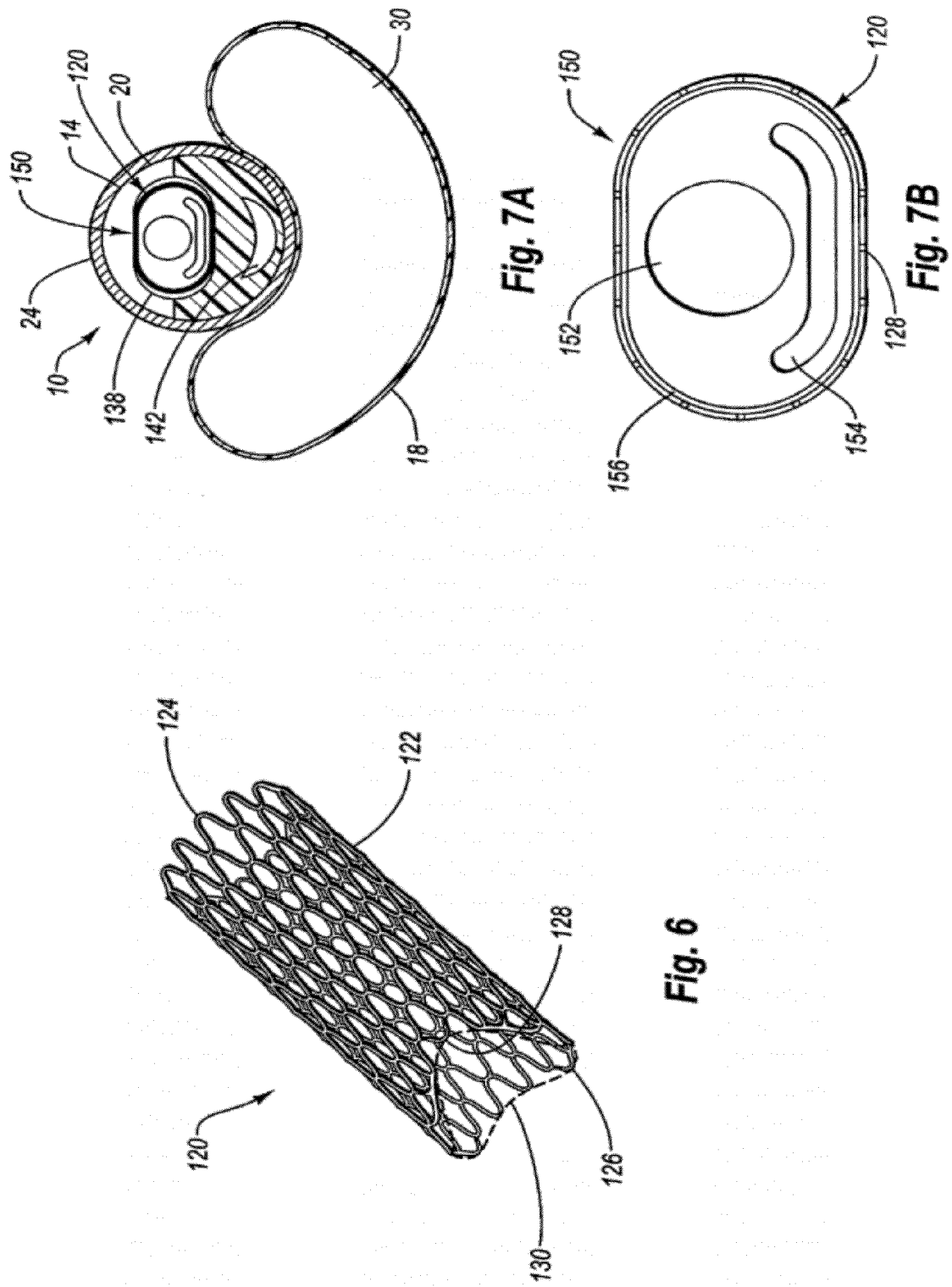

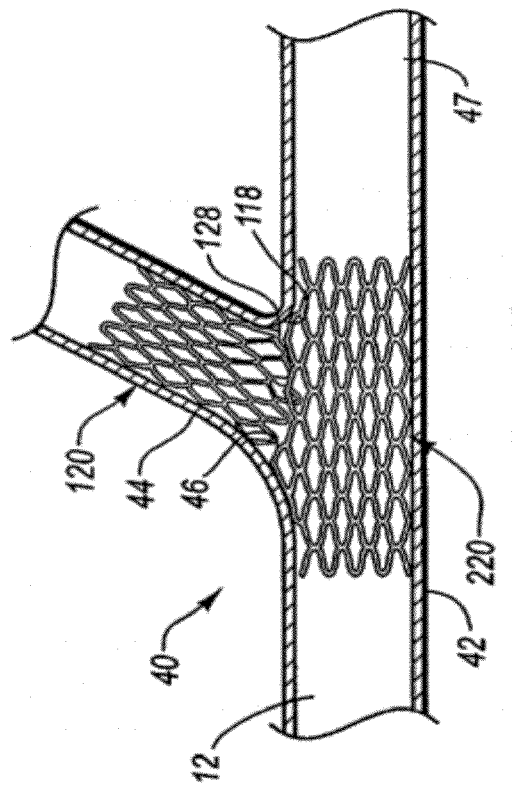
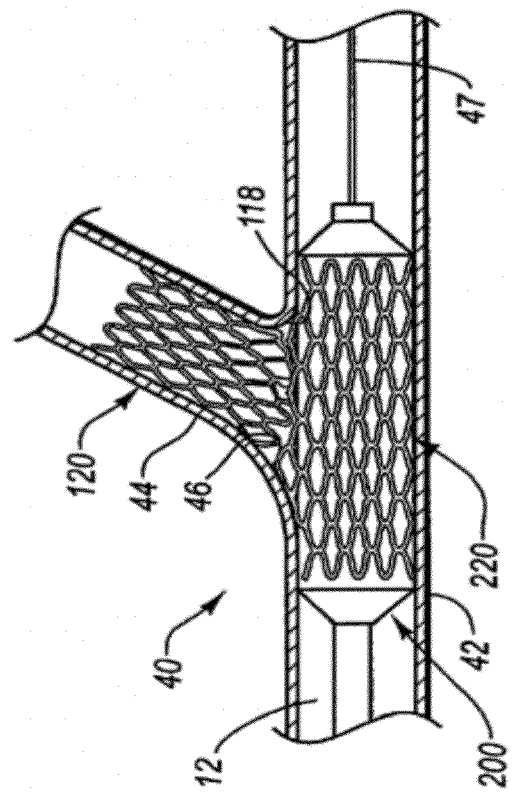

SYSTEM AND METHOD FOR DELIVERING A STENT TO A BIFURCATED VESSEL

CROSS-REFERENCE TO RELATED APPLICATIONS

This application claims the benefit of the U.S. Provisional Patent Application No. 60/780,752, filed Mar. 9, 2006, and entitled "Contoured Stent and Delivery System with Novel Tip Design," which is incorporated herein by reference in its entirety.

BACKGROUND

1. Technology Field

The present invention generally relates to intravascular stent systems. In particular, the present invention relates to a stent delivery catheter system that facilitates the accurate positioning of a stent with respect to an ostium of a bifurcated body vessel.

2. The Related Technology

Angioplasty and stent implantation procedures are commonly employed to treat lesions or blockages that form within the vascular anatomy of a patient. During an angioplasty, or percutaneous transluminal coronary angioplasty ("PTCA") procedure, for instance, a guiding catheter is advanced through the vasculature of the patient to a desired point, such as the ostium of a predetermined coronary artery. A guidewire, positioned within a balloon catheter, is extended from a distal end of the guiding catheter into the patient's coronary artery until it penetrates and crosses a lesion to be dilated. The balloon catheter is then advanced through the guiding catheter and over the previously introduced guidewire, until it is properly positioned across the lesion.

Once properly positioned, the balloon is inflated to a predetermined size such that the stenosis of the lesion is compressed against the arterial wall, thereby expanding the passageway of the artery. The balloon is subsequently deflated, blood flow resumes through the dilated artery, and the balloon catheter is removed.

Occasionally, post-procedure restenosis, or reformation of the arterial blockage, occurs after the PTCA procedure has been performed. Or, a dissection in the blood vessel wall caused by the balloon angioplasty procedure may occur. In addition, elastic recoil and remodeling of the vessel wall after the angioplasty procedure can result. To correct these side effects and strengthen the dilated area, physicians frequently implant an intravascular prosthesis, generally called a stent, inside the artery at the site of the lesion. During a stent implantation procedure, a stent is delivered in a contracted state on a balloon catheter to the desired location within a coronary artery.

Once properly positioned, the stent is expanded to a larger diameter via expansion of the balloon, which causes the stent to expand against the arterial wall at the lesion site. The balloon is then deflated and it and the catheter are withdrawn. The expanded stent remains in place within the artery at the site of the dilated lesion, holding the vessel open and improving the flow of blood therethrough. Stents have been successfully implanted in the z urinary tract, the bile duct, the esophagus and the tracheo-bronchial tree to reinforce those body organs, as well as implanted into the neurovascular, peripheral vascular, coronary, cardiac, and renal systems, among others.

Lesions are often located at or near a point of bifurcation in an artery or other body vessel. When treating such bifurcated lesions, it is common to first place a first guidewire in the main branch, then place a second guidewire, extending from the main branch, into the side branch of the vessel bifurcation. This is so because it is generally important to preserve the side branch and the main branch of the bifurcation.

Specifically, in some instances the above-described dilation via PTCA procedure causes plaque to be shifted from the treated main branch of the vessel bifurcation to the non-treated vessel side branch, thereby occluding the side branch. This effect is known as the "snowplow" effect. Prior placement of the second guidewire in the vessel side branch enables treatment of the side branch should it become occluded due to the snowplow effect.

Treatment of the side branch in this case often includes deployment of a stent therein. The stent is desirably placed in the vessel side branch and deployed so that its proximal end is disposed as close to the ostium, or side branch vessel opening, as possible.

Particularly, it is desired for a stent in a side branch to be positioned axially so as to cover the entirety of the side branch ostium. However, care must also be taken so as to avoid placing the stent such that it "overhangs" beyond the side branch ostium into the lumen of the main branch proximate the ostium. If such overhanging occurs, proper placement of a stent subsequently in the main branch could be compromised undesirably causing, among other things, inhibited blood flow through the stented region. At the same time, placing the stent too far distally into the side branch lumen prevents the stent from adequately covering the ostium, which can make the ostium region susceptible to further degradation or formation of stenoses.

As seen by the above discussion, therefore, it is sometimes necessary in the treatment of lesions at a bifurcated vessel site to deploy a stent in the side branch of the bifurcation. It is paramount, however, to accurately place the stent axially within the side branch so as to avoid the problems described above.

Yet another challenge relating to the placement of a stent relates to the difficulty encountered in maneuvering the stent during its intraluminal transit to the stent deployment site. Particularly, advancement of the stent via the typically tortuous vessel path is made more difficult by the inability to adequately control the rotation of the stent deployment assembly relative to the main branch and side branch of the bifurcated vessel.

In greater detail, during advancement of a catheter along a predisposed guidewire as described earlier, the bifurcation stent deployment assembly, which is coupled with the catheter to support and transport the bifurcation stent in a collapsed state, is not rotatably controlled. Hence, it is often necessary to rotate and reorient a distal portion of the catheter about its longitudinal axis in order to ensure proper alignment of the stent relative to the side branch before its deployment therein.

Unfortunately, transmitting a controlled rotation to the distal end of the catheter over the length of the flexible catheter shaft, however, had traditionally proven difficult. This difficulty is due in part to the complex anatomy of a coronary artery, which results in the flexible catheter shaft being unable to adequately transfer an imposed rotational torque to a distal portion of the catheter shaft where the stent deployment assembly is positioned. Instead, the elongated, flexible catheter shaft merely rotates at the proximal portion when twisted without transmitting the rotational torque distally to the stent deployment assembly in a consistent or satisfactory manner.

Accordingly, there is a need for a stent delivery system with improved alignment and orientation capabilities for aligning a distally positioned stent for deployment within the lumen of a body vessel. More particularly, a need exists for a stent delivery system capable of enabling precise axial and radial positioning of the stent for placement at a vessel bifurcation, for instance, so as to enable the ostium of such a bifurcation to be adequately covered by the stent while preventing undesirable overhang of the stent into proximate areas of the bifurcation.

BRIEF SUMMARY

The present invention has been developed in response to the above and other needs in the art. Briefly summarized, embodiments of the present invention are directed to a stent delivery catheter system for accurately positioning a stent in a bifurcated vessel. Advantageously, the system enables a proximal end of the stent to be positioned proximate the ostium of a side branch of the bifurcated vessel, an operation traditionally difficult to achieve using known systems.

In one embodiment, the system includes a catheter having a terminal portion and distal tip that is placed in a main branch of the vessel proximate the bifurcation. A fixed guidewire is attached to the distal tip. A port is defined in the terminal portion of the catheter. The port is aligned with an ostium of a side branch of the bifurcated vessel to allow the passage of a stent delivery device, such as a balloon catheter having a stent crimped thereon, into the side branch. Radiopaque bands are positioned on opposite ends of the port. A positioning balloon is included on a surface of the catheter opposite the port and is selectively inflatable to position the radiopaque bands adjacent the side branch ostium. The radiopaque bands are referenced to place the stent proximate the side branch ostium.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 2A and 2B are side views of a stent delivery catheter system having a positioning balloon in a deflated and inflated state, respectively, according to one embodiment;

FIG. 4A is a cross sectional side view of the stent delivery catheter system of FIG. 3A, taken along the line 4-4, showing various details thereof;

FIG. 4B is a cross sectional side view of a distal tip portion of the stent delivery catheter system, showing an alternative embodiment for placement and use of a fixed guidewire;

FIG. 5A-5H are a series successive side views showing use of the stent delivery catheter system of FIGS. 1A-4A in delivering a stent for deployment at a vessel bifurcation, according to one embodiment;

FIG. 6 is a perspective view of a stent having a contoured proximal end, suitable for deployment using one embodiment of the system described herein;

FIG. 7A is a cross sectional view of the stent delivery catheter system having a catheter lumen configured in accordance with one embodiment;

FIG. 7B is a cross sectional view of a stent delivery device configured for transit via the catheter lumen shown in FIG. 7A; and FIGS. 8A-8I are a series successive side views showing use of the stent delivery catheter system of FIG. 7A in delivering multiple stents for deployment at a vessel bifurcation, according to one embodiment.

DETAILED DESCRIPTION OF SELECTED EMBODIMENTS

Figure 1A:
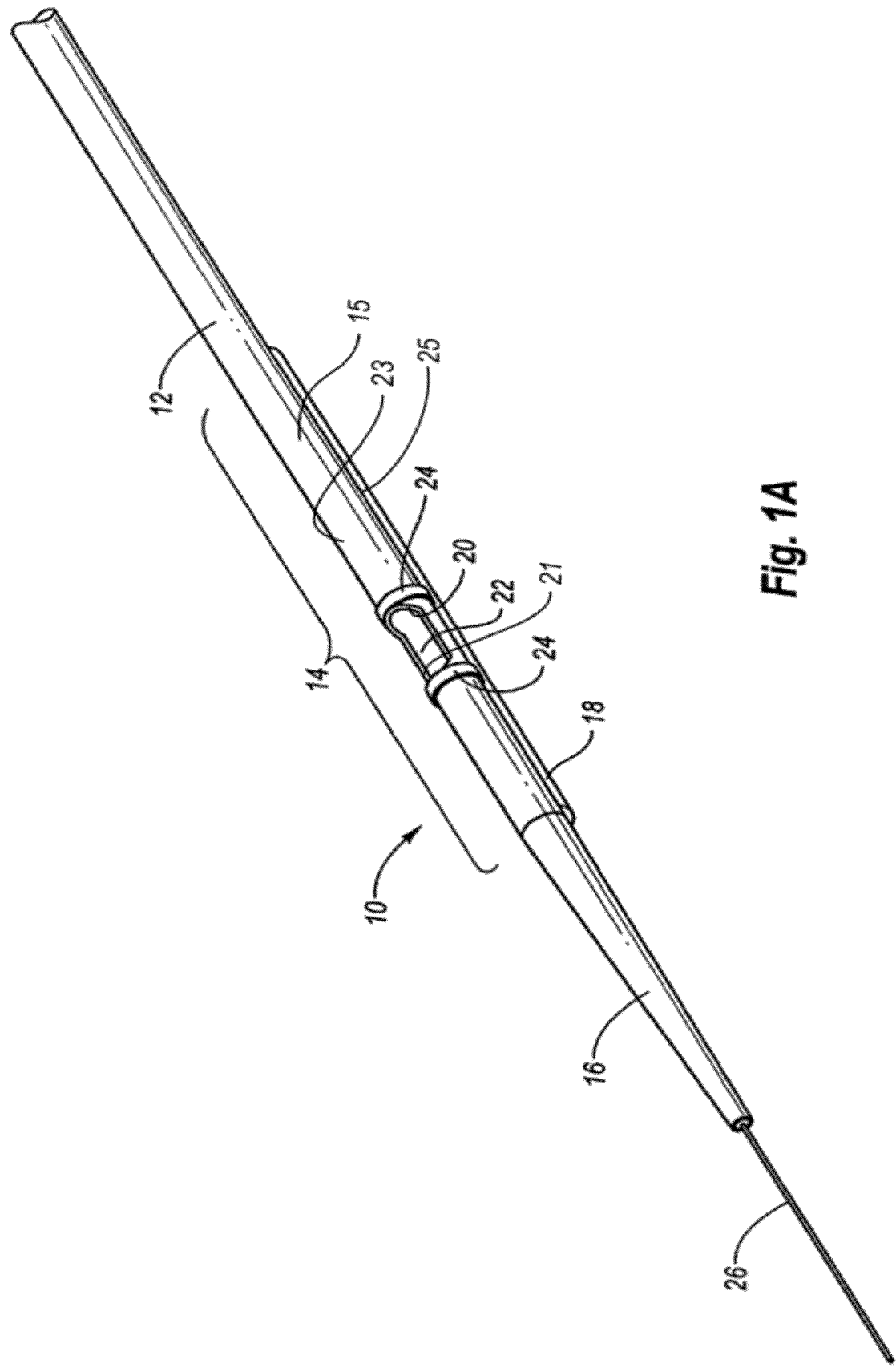
FIGS. 1A and 1B are perspective views of a stent delivery catheter system having a positioning balloon in a deflated and inflated state, respectively, according to one embodiment.

Reference will now be made to figures wherein like structures will be provided with like reference designations. It is understood that the drawings are diagrammatic and schematic representations of exemplary embodiments of the invention, and are not limiting of the present invention nor are they necessarily drawn to scale.

FIGS. 1A-8I depict various features of embodiments of the present invention, which is generally directed to a stent delivery catheter system for use in accurately deploying a stent in a bifurcated body vessel, such as a coronary artery, for instance. The stent delivery catheter system as disclosed herein enables the stent to be accurately positioned in a portion of the bifurcated vessel such that the stent is able to perform its intended function without causing complications related to improper placement.

As described herein, the stent delivery catheter system is employed in placing stents within the lumen of a coronary artery. However, this description is exemplary only, and it should be appreciated that embodiments of the present system can be employed for stent placement in a variety of body lumens, including the urinary tract, bile duct, esophagus and tracheo-bronchial tree, neurovascular, peripheral vascular, cardiac, and renal systems, among others. Also, as used herein, the term "stent" is understood to include a device that is intraluminally implanted within bodily vessels to reinforce collapsing, dissected, partially occluded, weakened, diseased or abnormally dilated or small segments of a vessel wall.

Reference is first made to FIGS. 1A-2B, which depict various aspects of a stent delivery catheter system ("system"), generally designated at 10, according to one embodiment. The system 10 includes a catheter 12 configured for intraluminal passage via a body vessel, and as such is sized for such passage, depending on the particular vessel dimensions. For example, for use in a coronary artery, the catheter has an outside diameter of approximately 1.3 to 1.7 mm, with a range of about 0.5 mm to about 10 mm, and an inside diameter of approximately 0.8 to 1.2 mm, with a range of about 0.4 mm to about 9.9 mm, though these dimensions are merely exemplary. For example, the stenting of non-coronary vessels may require catheter dimensions of a significantly larger magnitude than what would be required for stenting a coronary artery. Though the catheter 12 is cylindrical, other cross sectional shapes can also define the catheter shape.

The catheter 12 includes a distal terminal portion 14 and a distal tip 16. The terminal portion 14 has a peripheral sidewall 15. The distal tip 16 is tapered and includes a fixed guidewire 26 to assist in tracking the system 12 intraluminally toward the stent deployment location during use. In one embodiment, the fixed guidewire 26 extends a distance of approximately 20 to 40 mm from the distal tip 16, though this distance can be altered as needed for a particular application.

Figure 1B:
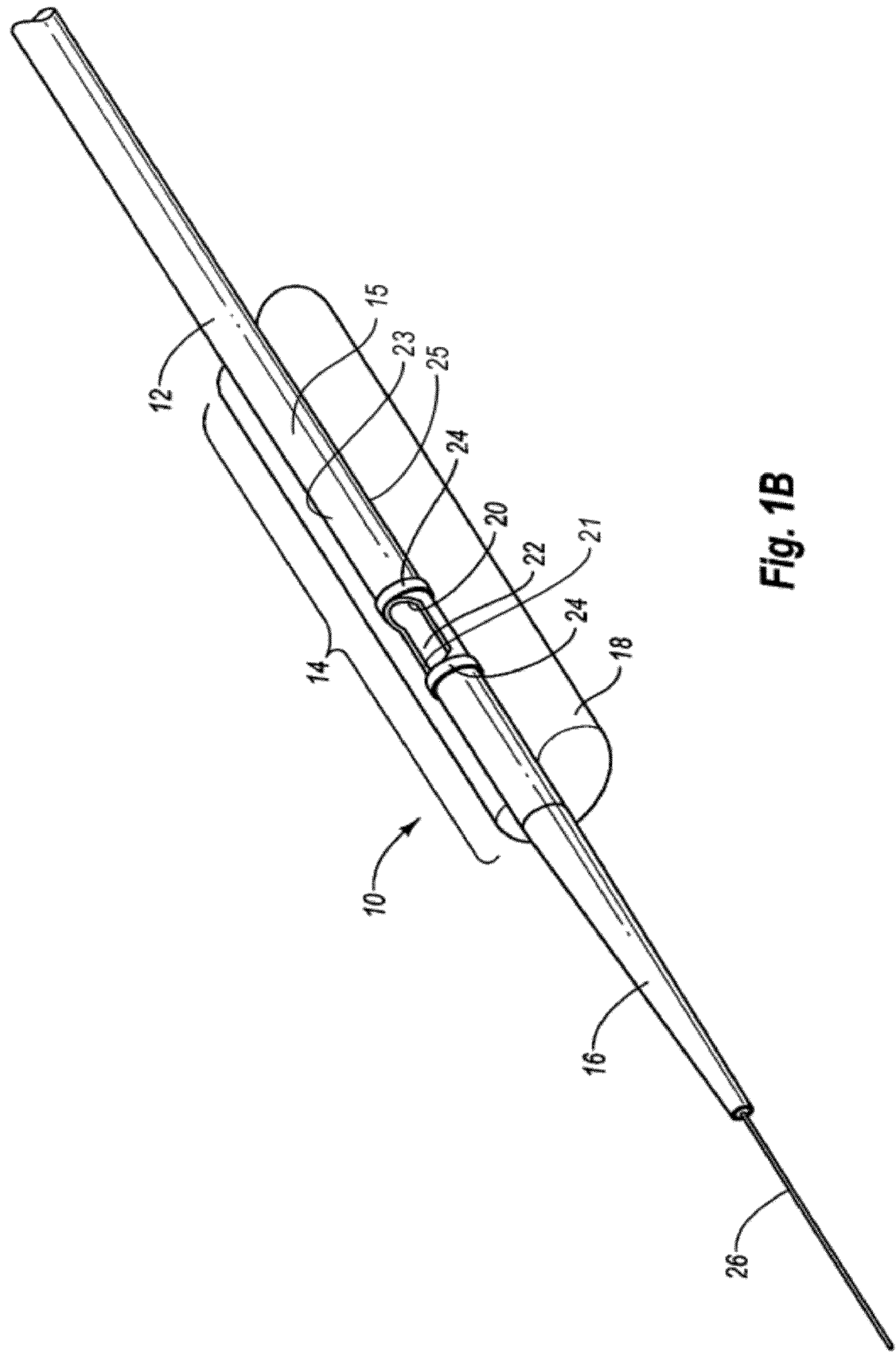

The terminal portion 14 of the catheter 12 includes a positioning balloon 18 longitudinally attached along the terminal portion. So attached, the positioning balloon 18 is disposed off-center, i.e., non-concentrically with respect to a longitudinal axis 36 (FIG. 4) of the system 10 and is selectively inflatable so as to expand as shown in FIGS. 1B and 2B. When not inflated, the positioning balloon 18 appears as shown in FIGS. 1A and 2A. In the depicted embodiment, no portion of the positioning balloon 18 completely encircles the terminal portion 14 of the catheter 12 about the longitudinal axis 36 (FIG. 4) whether inflated or not.

As best seen in FIG. 1B, when expanded the positioning balloon 18 has a kidney-bean cross sectional shape such that its dimensions in radially extending directions from the catheter 12 increase from its deflated state. This expansion in volume assists the positioning balloon 18 in securing the position of the system 10 within a vessel when used intraluminally, as will be described. Other cross sectional shapes of the positioning balloon 18 are also possible, as appreciated by one skilled in the art.

A cutout 20 is included in the terminal portion 14 of the catheter 12 so as to define a port 22. The cutout 20 comprises a through surface 21 extending through the peripheral sidewall 15 on a first lateral side 23 of the catheter opposite the point of attachment of the positioning balloon 18 on a second lateral side 25 of the catheter. As such, the through surface 21 defines the port 22. The port 22 defines an outlet from the interior of the catheter 12 for enabling the delivery of a stent delivery device, such as a balloon catheter, as will be described. The cutout 20 includes angled end portions and horizontally parallel side portions to define the port 22, though other shapes are also possible. In the present embodiment, the port 22 has a greater length of approximately 1.3 mm, a lesser length of approximately 0.9 mm, a depth from the catheter outer surface of approximately 0.5 mm, and a width of approximately 1.0 to 1.3 mm, though these dimensions can be varied according to catheter dimensions and the size of the stent delivery device to be passed therethrough.

Disposed adjacent the longitudinal ends of the port 22 are port position indicators, or markers, that indicate the position of the port 22 within the lumen of a vessel when viewed radiographically. In the present embodiment, the position indicators are implemented as annular, radiopaque ("RO") bands 24 that are disposed about the outer surface of the catheter 12 on either end of the port 22. Note that other suitable port position indicators could alternatively be implemented in other embodiments. The RO bands 24 are composed at least partially of a radiopaque material, including metals such as platinum, gold, and alloys thereof, plastics, polymers, other synthetic materials, etc.

Figure 3B:
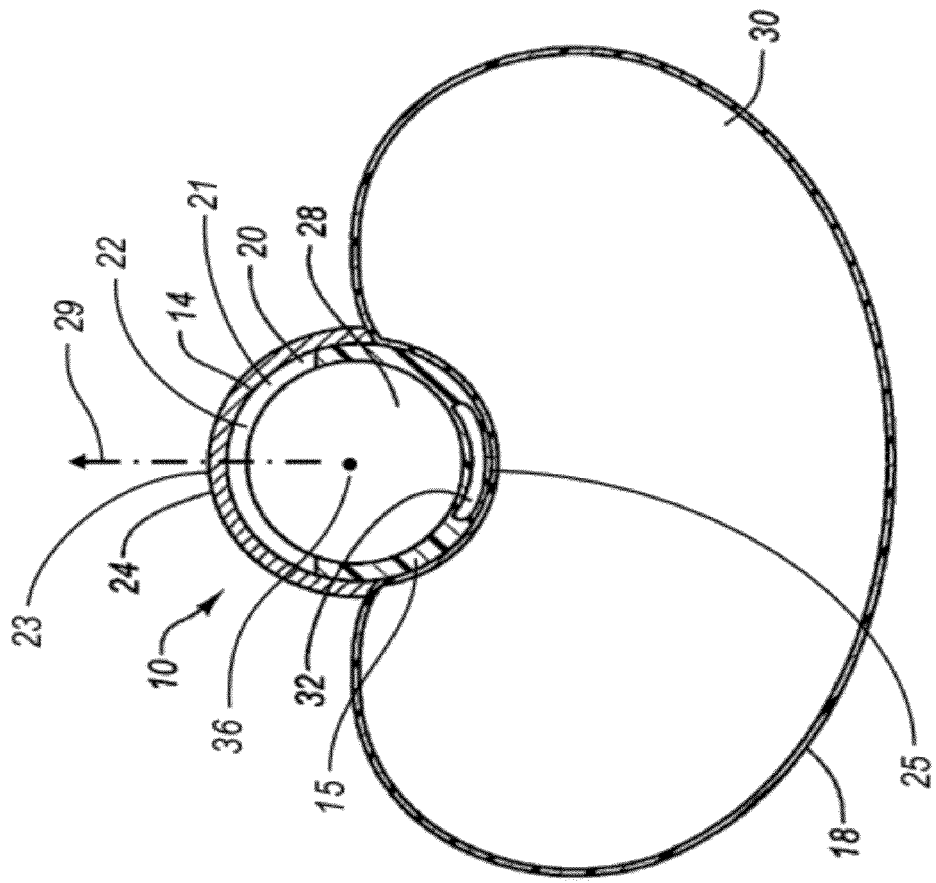
FIGS. 3A and 3B are cross sectional views of the stent delivery catheter system of FIGS. 2A and 2B taken along the lines 3A-3A and 3B-3B, respectively, showing the positioning balloon in a deflated and inflated state, according to one embodiment.
Figure 3A:
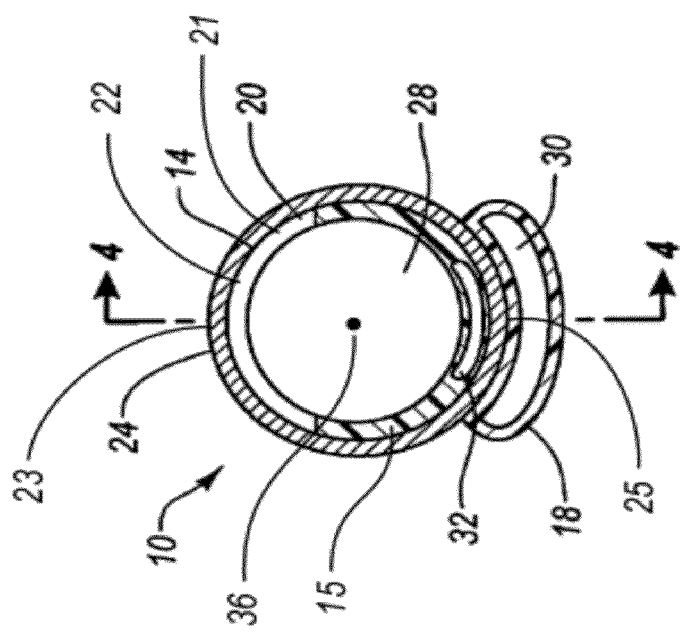

Together with FIGS. 1A-2B, reference is now made to FIGS. 3A-4B, which respectively show radial and axial cross sectional views of the system 10, according to one embodiment. In particular, a lumen 28 of the catheter 12 is shown bounded by the peripheral sidewall 15. The lumen 28 is sized according to particular need so as to both be able to travel intraluminally to the vessel bifurcation where the stent is to be placed and to enable passage therethrough of a stent delivery device. Again, though the cross sectional shape of the catheter lumen 28 is round, other shapes could be used according to need. As shown in FIGS. 3A and 3B, the port 22 communicates with the lumen 28 and faces outward from the longitudinal axis 36 of the catheter 12 in a radial direction denoted by arrow 29.

FIGS. 3A and 3B show the expansion of a volume 30 of the positioning balloon 18 that is achieved when the balloon is inflated in a manner to be described below. Though the inflated and deflated dimensions of the balloon can be varied according to the particular application, they are sufficient to enable intraluminal passage of the catheter 12 when deflated and securing of the catheter position within the vessel when inflated, as will be discussed further below. In the depicted embodiment, no portion of the expandable means (i.e., the positioning balloon 18) extends beyond any portion of the port 22 in the radial direction 29 during expansion of the expandable means. Note that the particular shape, length, width, etc., of the balloon 18 can be modified from what is shown in the accompanying figures while still residing within the scope of the present invention.

FIG. 4A shows that the fixed guidewire 26 is indeed affixed to an interior portion of the distal tip 16. In one embodiment, the length of portion of the fixed guidewire 26 extending from the distal tip 16 is approximately 20 to 40 mm. As its name implies, the fixed guidewire 26 is employed to assist in guiding the system 10 to a vessel location, where a stent is to be deployed. In one embodiment, the distal end of the fixed guidewire 26 is flexible and can include an atraumatic tip that aids in guiding the system 10 during intraluminal passage. Such atraumatic tips typically include a flexible coil (not shown) disposed about a distal portion of the fixed guidewire, which terminates with a solder ball or other atraumatic feature (not shown) at the tip of the fixed guidewire. The fixed guidewire 26 is composed of a suitable material, such as stainless steel, NiTiNOL, plastics, polymers, and suitable combinations of these materials, for instance.

Though not used in the presently discussed system configuration, FIG. 4B illustrates another possible configuration for the fixed guidewire 26, wherein the distal tip 16 defines an open end and a hollow interior so as to define a lumen 17 therethrough that is in communication with the lumen 28 of the catheter 12. In this configuration, the system could be configured such that an additional guidewire (not shown) is passed through the lumen 17 of the distal tip 16 and the lumen 28 of the catheter 12 to further guide the system 10 during intraluminal transit. In such a case, the fixed guidewire could be retained or omitted, according to need.

An inflation lumen 32 is shown disposed within the catheter lumen 28 and is in fluid communication with a conduit 34, which serves as an inlet/outlet for the positioning balloon 18. Via the conduit 34, the inflation lumen 32 can supply to or remove from the balloon 18 a fluid—suitable gas or liquid—useful for inflating/deflating the balloon during system operation. Note that the inflation arrangement shown and described herein, however, is merely exemplary; various other inflation/deflation configurations can be used with the present system. For example, the inflation lumen can be external to the catheter 12 or integrated with the catheter wall. Also, separate inlet and outlet conduits can be defined with the balloon. In the present embodiment, the inflation lumen is crescent-shaped defined so as to minimize it cross sectional catheter profile. These and other modifications are therefore considered part of the present invention.

Figure 5E:
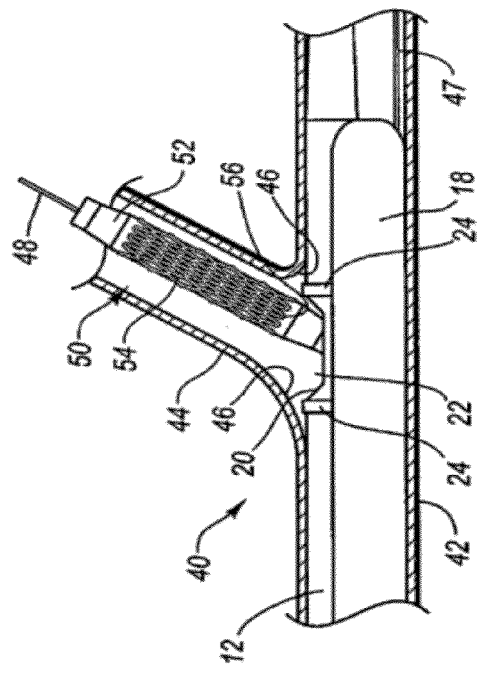

Reference is now made to FIGS. 5A-5H in describing operation of the stent delivery catheter system 10 in facilitating the accurate placement of a stent at a bifurcated vessel location, such as the vessel 40 shown in FIG. 5A, including a main branch 42 and side branch 44 that branch at a point of bifurcation 45. The vessel side branch 44 defines an opening, or ostium, 46 at the bifurcation 45. Note that the particular size and shape of the vessel branches, bifurcation, and ostium are dependent on the particular type and structure of vessel being stented. As such, the vessel and respective branches shown here are merely exemplary of the broader range of vessel configurations that can benefit from the present invention. By way of example here, the vessel 40 shown here is a coronary artery.

As shown in FIG. 5A, a first guidewire 47 is first inserted into the main branch 42 of the vessel 40 past the bifurcation 45 to ensure that the main branch can be accessed and stented, if necessary, after stenting of the side branch is complete. In FIG. 5B, the system 10 is introduced into the patient and intraluminally advanced through the vasculature until the distal tip 16 has passed the bifurcation 45. Note that the positioning balloon 18 is deflated during this phase of system advancement through the vasculature.

As shown in FIG. 5B, the terminal portion 14 of the catheter 12 can be adjusted until the RO bands 24 indicate (via remote radiographic imaging or the like) that the port 22 is aligned with the ostium 46 of the vessel side branch 44. The alignment achieved by the port 22 is both a radial and an axial, i.e., longitudinal, alignment with the side branch ostium 46, so as to enable delivery of a stent delivery device into the vessel side branch 44. Note that, because alignment with the vessel side branch ostium 46 is performed by the system 10, radial and axial alignment of the stent delivery device (FIG. 5D) itself is minimized. To assist with alignment of the port 22 with the side branch ostium 46, an additional RO marker (not shown) could be included in a longitudinal direction on a surface of the catheter 12 opposite the port. This marker could then be radiographically detected (e.g. via fluoroscopy) so as to determined when the port is properly aligned with the ostium.

As shown in FIG. 5C, a second guidewire 48 is passed through the catheter 12 and terminal portion 14 of the system 10, exiting the port 22 and extending into the vessel side branch 44. In FIG. 5D, the second guidewire is used to position a stent delivery device, such as a balloon catheter 50, having a balloon 52 with a stent 54 crimped thereon, into the vessel side branch 44. Again, the catheter 12 and port 22 are sized and configured to enable the stent-equipped balloon catheter 50 to pass through the catheter and port 22, past the ostium 46, and into the vessel side branch 44. Because the port 22 is already aligned radially and axially with the ostium 46, passage of the balloon catheter 50 is readily performed.

Note that placement of the second guidewire 48 into the vessel side branch 44 can alternatively be performed before the system 10 is inserted into the main branch 42, if desired, so as to assist in aligning the port 22 of the system with the side branch ostium 46. Also note that the balloon catheter passes through the port 22 and enters the vessel side branch 44 at an angle with respect to the longitudinal axis 36 (FIG. 4) of the catheter 12.

Figure 5F:
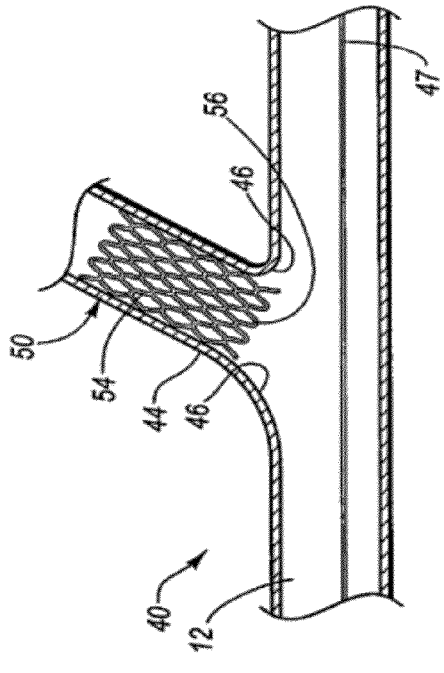

As shown in FIG. 5E, once the balloon catheter 50 has been inserted into the vessel side branch 44, the positioning balloon 18 of the system 10 is inflated, which causes the terminal portion 14 of the catheter 12 to be pressed against the inner wall of the vessel main branch 42 and the RO bands 24 to be brought into proximate position with the side branch ostium 46. With the RO bands 24 proximately positioned with respect to the side branch ostium 46—in some cases being in proximity so as to touch the ostium—the balloon catheter 50 can be axially maneuvered within the vessel side branch 44, as shown in FIG. 5F, so that a proximal end 56 of the stent 56 is positioned in proximity with the ostium 46, as desired. Note that the RO bands in one embodiment can be encapsulated, if desired, so as to avoid their directly pressing against a portion of the vessel wall.

Figure 5G:
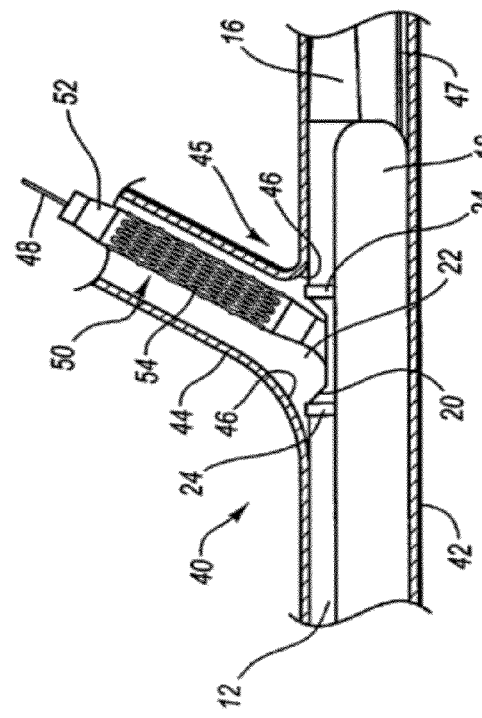
Figure 5H:
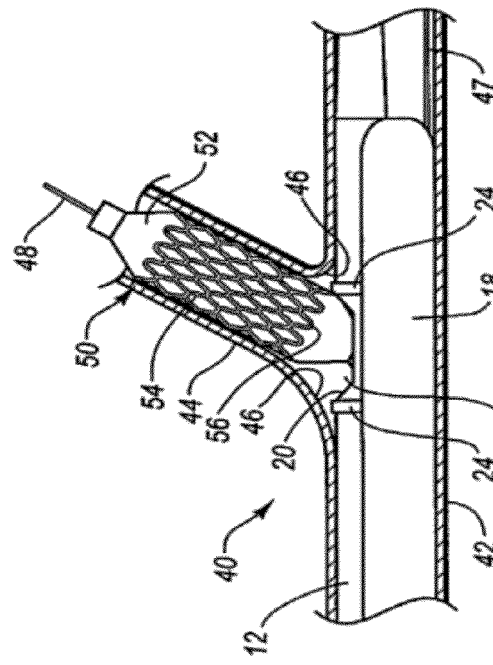

Because the vessel side branch ostium 46 is not readily identifiable radiographically, the RO bands 24—which are readily identifiable radiographically and which are placed proximate the ostium—are used to accurately position the stent proximal end 56 with respect to the ostium. Once positioned as desired, the stent 54 is deployed by inflating the balloon 52 of the balloon catheter 50 within the vessel side branch 44, as shown in FIG. 5G.

Upon deployment of the stent 54, the balloon catheter 50 is removed via the port 22 and catheter 12 of the system 10. The positioning balloon 18 is then deflated and the system 10 is removed from the main branch 42 of the vessel 40. The first guidewire 47 can then be removed or used to position another stent (not shown) in the main branch 42.

As can be seen from the above discussion, therefore, the positioning balloon described above serves as one exemplary expandable means for selectively positioning a position indicator, such as an RO band, proximate an ostium of a bifurcated vessel, in connection with deploying a stent therein. Note, however, that the positioning balloon serves as only one example of such a means. Indeed, various other devices, such as a mechanically expandable device, may be acceptably employed as a means for selectively positioning a position indicator in accordance with the principles of the present invention. The present invention should therefore not be limited to any one embodiment.

In addition to the advantages described above, embodiments of the present invention further reduce the risk of snowplow effects as a result of treating the vessel side branch as the system 10 substantially occupies the entirety of the vessel main branch lumen proximate the bifurcation during the stenting procedure.

Reference is now made to FIGS. 6-7B in describing use of the present system 10 to deploy a stent having a contoured proximal end. FIG. 6 shows such a contoured stent, generally indicated at 120, which is deployable for use with an ostium of a side branch having a curvilinear profile, e.g. a saddle-shaped profile—typical of many side branches of bifurcated vessels.

As shown, the contoured stent 120 includes a generally cylindrical body 122 defining a distal end 124 and a proximal end 126. The body 122 of the stent is composed in the present embodiment of an interlocking lattice of small strand wire composed of a suitable material, such as stainless steel. The interlocking lattice of the stent body 22 is expandable for deployment within the lumen of a bifurcated vessel side branch, as will be described. Notwithstanding its characterization herein, it is appreciated that the stent body can be configured in other ways from what is described herein while still residing within the scope of the claims.

FIG. 6 shows that the proximal end 126 of the stent 120 includes an inset portion 128. The inset portion 128 generally defines a parabolic shape that extends toward the distal end 124 of the stent 120 a predetermined distance. As such, the inset portion 128 represents the most distal portion of the proximal end 126 of the stent 120. In greater detail, the outermost portions of the interlocking wire lattice of the stent body 122 body located at the proximal end 126 thereof generally define a three-dimensionally contoured profile 130. The contoured profile 130 is configured to at least approximately match the three-dimensionally curvilinear profile of the exemplary ostium of the vessel side branch so as to acceptably cover all portions of the ostium.

Note that the particular contour of the proximal end of the stent can be altered in shape and configuration from what is described herein so as to acceptably match ostiums of other vessels, both bifurcated and non-bifurcated, having other curvilinear shapes. For example, the profile of the stent proximal end in one embodiment can include two or more inset portions to acceptably match a similarly contoured vessel ostium when the stent is deployed in the lumen of the vessel. As such, the presently described embodiments should not be construed to limit the present invention in any manner. Further details regarding the contoured stent 120 can be found in the U.S. patent application entitled, "STENT HAVING CONTOURED PROXIMAL END," filed Mar. 8, 2007, (attorney docket no. 17066.33.1), which is incorporated herein by reference in its entirety.

FIG. 7A shows that, as before, the system 10 includes a terminal portion 14 having a catheter lumen 138 and an inflation lumen 142. However, in this embodiment, the catheter lumen 138 has an oblong cross sectional shape for receiving therein a similarly cross sectionally shaped stent delivery device, such as a balloon catheter 150 shown in FIG. 7B. In particular, the balloon catheter 150 includes a guidewire lumen 152 for guiding the catheter via a guidewire, and an inflation lumen 154 for selectively inflating a balloon 156. The balloon catheter 150 is oblong-shaped such that when the contoured stent 120 is crimped about the balloon 156 as shown in FIG. 7B, it also assumes an oblong cross sectional shape. The cross sectional shape of both the catheter lumen 138 and balloon catheter 150 can be varied to have other shapes, as may be appreciated by one skilled in the art. Also, other stent delivery devices, apart from that shown at 150 in FIG. 7B, can alternatively be used with the system 10 shown in FIG. 7A.

Note that, as shown in FIG. 7B, the contoured stent 120 is loaded on to the balloon 156 of the balloon catheter 150 such that the inset portion 128 is disposed at the bottom of the balloon, as seen in the view given in FIG. 7B. This positioning ensures that the stent 120 is properly oriented with respect to the ostium of the side branch vessel when deployed.

Figure 8A:
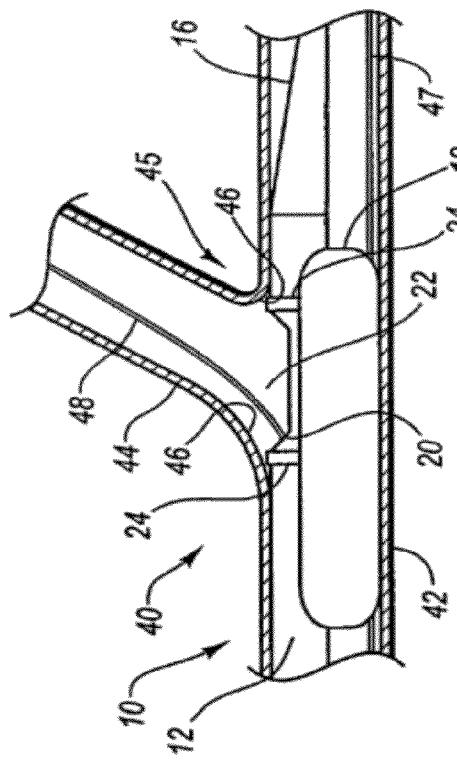
Figure 8B:
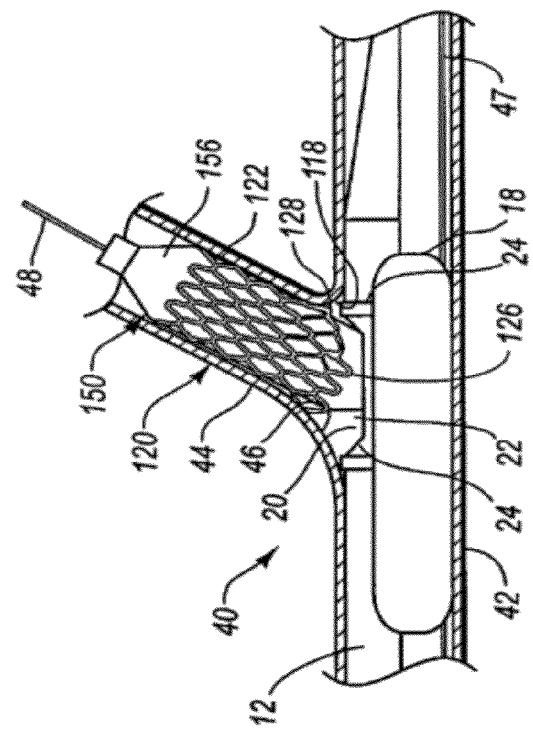
Figure 8C:
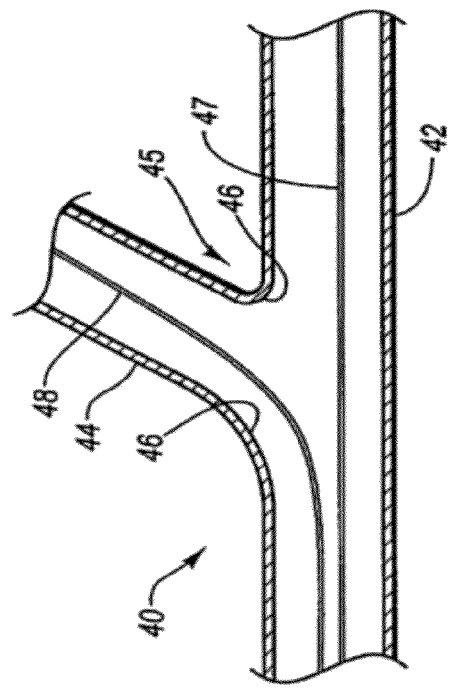

Reference is now made to FIG. 8A-8I. Deployment of the contoured stent in the vessel side branch 44 according to one embodiment proceeds by first inserting the first and second guidewires 47 and 48 into the main branch 42 and side branch 44, respectively (FIG. 8A). The system 10 is then moved into position such that the port 22 is aligned with the ostium 46 of the side branch 44 (FIG. 8B). The positioning balloon 18 of the terminal portion is then inflated. The balloon catheter 150 is advanced on the second guidewire 48 via the catheter lumen 138 of the catheter 12 and terminal portion 14 in the orientation shown in FIG. 7B until it passes through the port 22 and into side branch 44 (FIG. 8C).

The balloon catheter 150 is adjusted distally as in previous embodiments to axially align the proximal end 126 of the stent 120 with the ostium 46. Note that substantial to complete coverage of the ostium 46 by the stent proximal end 126 is possible because of the curvilinear profile defined by the proximal end that matches the curvilinear profile of the ostium. Radial alignment of the inset portion 128 of the stent proximal end 126 with a corresponding inset portion 118 of the curvilinear ostium 46 is achieved ensured by virtue of the predetermined alignment of both the port 22 of the system 10 with the ostium 46 as well as the orientation of the inset portion of the stent as crimped on the balloon 156 in the manner shown in FIG. 7B.

Figure 8D:
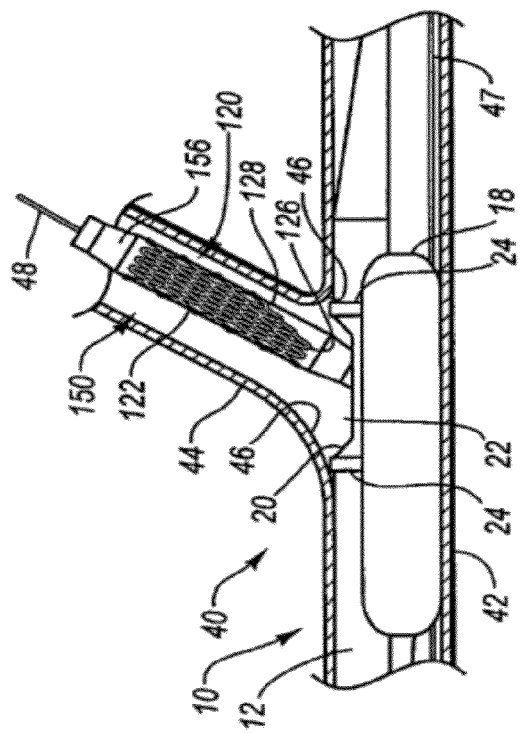
Figure 8F:
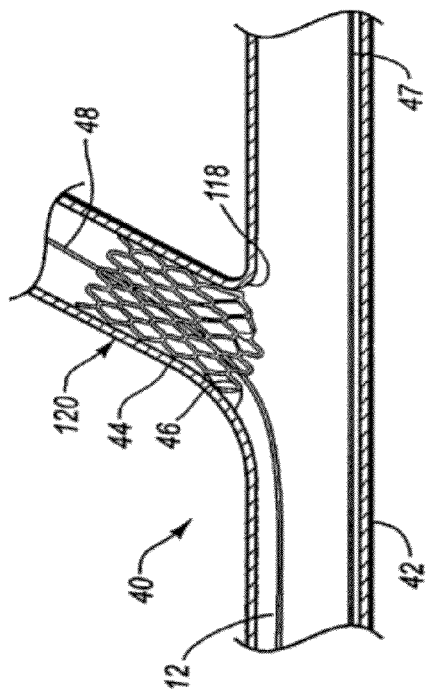
Figure 8E:
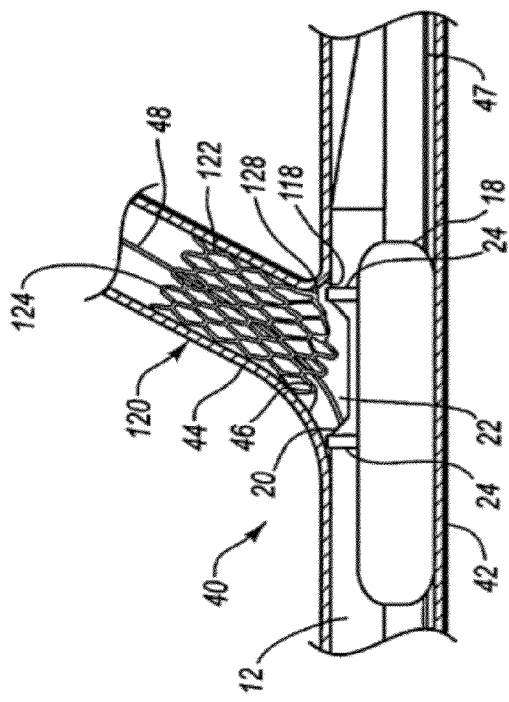

Once properly aligned, the contoured stent 120 is deployed against the walls of the vessel side branch 44 by inflating the balloon 156 via the inflation lumen 142 (FIG. 7B) of the balloon catheter (FIG. 8D). As a result, the contoured stent 120 is positioned as shown in FIG. 8E. The system 10 is then withdrawn from the vessel main branch 42 (FIG. 8F), as is the second guidewire 48 from the side branch 44.

Figure 8G:
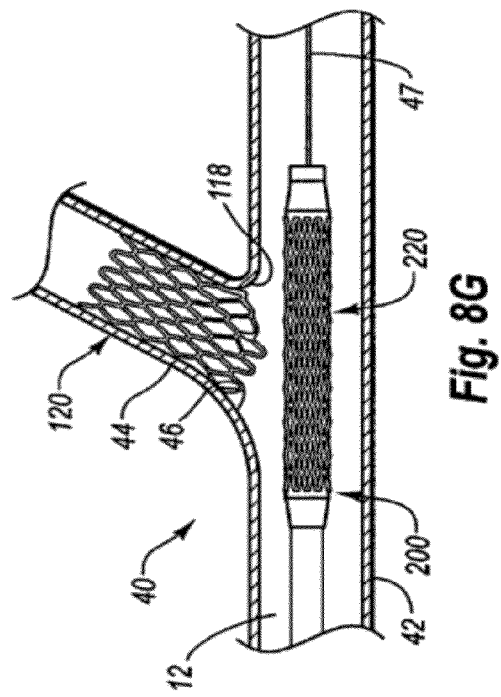

As shown in FIG. 8G, another balloon catheter 200 is then inserted into the vessel main branch 42, having a standard stent 220 crimped thereon. After proper alignment, the stent 220 is deployed against the main branch vessel wall proximate the ostium 46 of the vessel side branch 44 (FIG. 8H). The balloon catheter 200 is then withdrawn. As a result the bifurcated vessel is stented such that the ostium 46 of the vessel side branch 44 is substantially covered by the contoured stent 120 without the contoured stent extending into the lumen of the main branch 44 so as to interfere with placement of the stent 220.

The present invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A system for delivering a stent to a bifurcated vessel, the system comprising:
    a stent delivery catheter having an outer perimeter, the stent delivery catheter comprising:
        an inflation lumen;
        a guidewire lumen;
        a balloon disposed on the outer perimeter and in fluid communication with the inflation lumen;
    and a stent disposed on the balloon;
    a catheter configured for insertion into a first branch of the bifurcated vessel, the catheter comprising a shaft including a distal terminal portion and a tapered distal tip extending along a longitudinal axis;
    an aperture through a lateral side of the terminal portion of the shaft of the catheter, the aperture defining a port, the port being sized so as to allow passage therethrough of the stent delivery device configured to place the stent proximate an ostium of a second branch of the bifurcated vessel, the port facing outward from the longitudinal axis of the catheter in a first radial direction;
    at least one position indicator included on the terminal portion of the catheter proximate the port; and
    expandable means for selectively positioning the at least one position indicator proximate an ostium of the bifurcated vessel, the expandable means being positioned on the lateral side of the terminal portion of the shaft of the catheter opposite the port, no portion of the expandable means extending beyond any portion of the aperture in the first radial direction during expansion of the expandable means.

2. The system for delivering the stent as defined in claim 1, wherein the system is configured such that the port is aligned with a side branch of the bifurcated vessel when the catheter is disposed in a main branch of the bifurcated vessel so that the stent can be delivered to the side branch of the bifurcated vessel through the port.

3. The system for delivering the stent as defined in claim 1, wherein the at least one position indicator is configured to be referenced when positioning a proximal end of the stent with respect to the ostium of the second branch.

4. The system for delivering the stent as defined in claim 1, wherein the at least one position indicator comprises two position indicators positioned proximate opposite ends of the port.

5. The system for delivering the stent as defined in claim 4, wherein the two position indicators are radiopaque.

6. The system for delivering the stent as defined in claim 1, wherein the port is configured such that the stent delivery device extends through the port at an angle with respect to the longitudinal axis of the catheter when the stent delivery device is positioned through the port.

7. The system for delivering the stent as defined in claim 1, wherein the expandable means is non-concentrically positioned with respect to the longitudinal axis of the catheter.

8. The system for delivering the stent as defined in claim 1, wherein the expandable means is selectively inflatable via an inflation line that extends substantially parallel to the catheter.

9. The system for delivering the stent as defined in claim 1, wherein the expandable means comprises a balloon that is affixed to the lateral side of the terminal portion of the catheter opposite the port.

10. The system for delivering the stent as defined in claim 1, further comprising a guidewire that is affixed to the distal tip of the terminal portion of the catheter.

11. The system for delivering the stent as defined in claim 1, wherein the at least one position indicator is positioned adjacent the port so as to contact the ostium when the expandable means is expanded.

12. The system for delivering the stent as defined in claim 1, wherein no portion of the expandable means completely encircles the terminal portion of the catheter about the longitudinal axis.

13. The system for delivering the stent as defined in claim 1, wherein the aperture comprises a through surface extending through the peripheral sidewall to define the port, and
wherein no portion of the positioning balloon extends beyond the through surface in the first radial direction during expansion of the positioning balloon.

14. The system for delivering the stent as defined in claim 1, wherein the expandable means extends from a proximal end to a distal end and encompasses less than an entire circumference of the catheter along a longitudinal length from the proximal end to the distal end of the expandable means.

15. The system for delivering the stent as defined in claim 1, wherein the expandable means extends from a proximal end to a distal end and encompasses more than a majority of an entire circumference of the catheter along a longitudinal length from the proximal end to the distal end of the expandable means.

16. A stent delivery catheter system, comprising:
a positioning catheter having a distal terminal portion configured for placement in a main branch of a bifurcated vessel and a shaft having a peripheral sidewall bounding a lumen extending along a longitudinal axis, the peripheral sidewall of the shaft having an aperture extending therethrough on a first lateral side of the positioning catheter, the aperture defining a port that communicates with the lumen, the port facing outward from the longitudinal axis in a first radial direction,
a stent delivery catheter having an outer perimeter, the port through the peripheral sidewall of the shaft of the positioning catheter being sized and configured to allow passage therethrough of the stent delivery catheter into a side branch of the bifurcated vessel for placing a stent proximate an ostium of the side branch, the stent delivery catheter comprising:
an inflation lumen;
a guidewire lumen;
a balloon disposed on the outer perimeter and in fluid communication with the inflation lumen;
and a stent disposed on the balloon;
a tapered distal tip attached to the terminal portion of the positioning catheter, the distal tip including a fixed guidewire;
first and second radiopaque markers positioned adjacent the port; and
an inflatable positioning balloon attached to the positioning catheter, the positioning balloon being configured to selectively position the first and second radiopaque markers proximate the ostium of the side branch so as to provide a reference for positioning the stent in the side branch, the positioning balloon being positioned on a second lateral side of the terminal portion of the positioning catheter opposite the port, such that the inflatable positioning balloon extends from a proximal end to a distal end and no portion of the inflatable positioning balloon extending beyond any portion of the aperture in the first radial direction during expansion of the inflatable positioning balloon.

17. The system as defined in claim 16, wherein the positioning balloon is off-center with respect to the longitudinal axis of the positioning catheter.

18. The system as defined in claim 17, wherein the positioning balloon is attached to the terminal portion of the positioning catheter opposite the port.

19. The system as defined in claim 18, wherein the port is in communication with a lumen of the positioning catheter, and wherein the stent delivery catheter is configured to track via the lumen of the positioning catheter.

20. The system as defined in claim 19,
wherein the stent is positioned with respect to the radiopaque markers so as to allow a proximal end of the stent to be positioned proximate the ostium of the side branch.

21. The system as defined in claim 20, wherein the stent is configured to be positioned so as to not overhang into the main branch of the bifurcated vessel.

22. The system as defined in claim 21, wherein the radiopaque markers comprise annular bands positioned about the terminal portion of the positioning catheter on opposite ends of the port.

23. The stent delivery catheter system as defined in claim 16, wherein no portion of the positioning balloon completely encircles the terminal portion of the positioning catheter about the longitudinal axis.

24. A stent delivery catheter system, comprising:
a stent delivery catheter having an outer perimeter, the stent delivery catheter comprising:
an inflation lumen;
a guidewire lumen;
a balloon disposed on the outer perimeter and in fluid communication with the inflation lumen; and
a stent disposed on the balloon, the stent having a generally cylindrical body defining a distal end and a proximal end, the stent including an inset portion at the proximal end that generally defines a parabolic shape extending toward the distal end a predetermined distance; and
a positioning catheter having a distal terminal portion configured for placement in a main branch of a bifurcated vessel, the positioning catheter comprising:
a shaft having a peripheral sidewall extending along a longitudinal axis, the shaft comprising:
an inflation lumen; and a catheter lumen that receives the stent delivery catheter therein, the catheter lumen defining a cross sectional shape that corresponds to the outer perimeter of the stent delivery catheter;

a tapered distal tip attached to the terminal portion of the positioning catheter, the distal tip including a fixed guidewire;

a port defined by a through surface of the peripheral sidewall, the port extending through the peripheral sidewall of the shaft on a first lateral side of the terminal portion of the positioning catheter so as to communicate with the catheter lumen, the port facing outward from the longitudinal axis of the positioning catheter in a first radial direction, the port being sized and configured to allow passage therethrough of the stent delivery catheter into a side branch of the bifurcated vessel for placing the stent proximate an ostium of the side branch;

first and second radiopaque markers positioned adjacent the port; and a positioning balloon in fluid communication with the inflation lumen of the positioning catheter, the positioning balloon being inflatable for selectively positioning the first and second radiopaque markers, the radiopaque markers being configured to be positioned proximate the ostium of the side branch so as to provide a reference for positioning the stent in the side branch, the positioning balloon being positioned on the shaft on a second lateral side of the terminal portion of the positioning catheter opposite the port, no portion of the positioning balloon extending in the first radial direction beyond the through surface of the peripheral sidewall that defines the port during expansion of the positioning balloon.

25. The system as defined in claim 24, wherein the stent includes a proximal end having a curvilinear profile configured to at least approximately match a curvilinear profile of the ostium.

26. The system as defined in claim 24, wherein a predetermined portion of the stent is positioned adjacent a predetermined portion of the outer perimeter of the stent delivery catheter before transit through the positioning catheter of the system.

27. The stent delivery catheter system as defined in claim 24, wherein no portion of the positioning balloon completely encircles the terminal portion of the positioning catheter about the longitudinal axis.

28. A stent delivery catheter system, comprising:
a positioning catheter having a distal terminal portion configured for placement in a main branch of a bifurcated vessel, the positioning catheter comprising:
a shaft having a peripheral sidewall extending along a longitudinal axis, the shaft comprising:
a first inflation lumen;
a catheter lumen;
a tapered distal tip attached to the terminal portion, the distal tip including a fixed guidewire;
a port defined by a through surface extending through the peripheral sidewall of the shaft on a first lateral side of the terminal portion so as to communicate with the catheter lumen, the port facing outward from the longitudinal axis in a first radial direction; and
first and second radiopaque markers positioned adjacent the port; and
a positioning balloon on the shaft in fluid communication with the first inflation lumen, the positioning balloon being inflatable for selectively positioning the first and second radiopaque markers, the positioning balloon being positioned on a second lateral side of the shaft of the positioning catheter opposite the port, no portion of the positioning balloon extending in the first radial direction beyond the through surface of the peripheral sidewall that defines the port during expansion of the positioning balloon; and
a stent delivery catheter received within the catheter lumen of the positioning catheter, the stent delivery catheter having an outer perimeter, the stent delivery catheter comprising:
a second inflation lumen;
a guidewire lumen;
a delivery balloon disposed on the outer perimeter and in fluid communication with the inflation lumen; and
a stent disposed on the delivery balloon, the stent having a generally cylindrical body defining a distal end and a proximal end, the stent including an inset portion at the proximal end that generally defines a parabolic shape extending toward the distal end a predetermined distance;
wherein the port of the positioning catheter is sized and configured to allow passage therethrough of the stent delivery catheter into a side branch of the bifurcated vessel for placing the stent proximate an ostium of the side branch; and
wherein the radiopaque markers are configured to be positioned proximate the ostium of the side branch so as to provide a reference for positioning the stent delivery catheter in the side branch.

* * * * *